US005815831A

United States Patent [19]

De Wan

[11] Patent Number: 5,815,831

[45] Date of Patent: Oct. 6, 1998

[54] HEADWEAR WITH SUNSHIELD

[76] Inventor: Thomas De Wan, 3200 Bayou Placido Blvd., NE., St. Petersburg, Fla. 33703

[21] Appl. No.: 504,926

[22] Filed: Jul. 20, 1995

[51] Int. Cl.[6] ................................ A61F 9/00; A42B 1/00

[52] U.S. Cl. .................................................... 2/10; 2/195.1

[58] Field of Search ................................ 2/195.1, 195.2, 2/195.3, 195.4, 195.6, 195.5, 195.7, 200.1, 10

[56] References Cited

U.S. PATENT DOCUMENTS

| | | | |
|---|---|---|---|
| 1,022,153 | 4/1912 | Pethybridge | 2/195.2 |
| 3,247,523 | 4/1966 | Lipkin | 2/195.3 |
| 4,268,918 | 5/1981 | Lee | 2/195.1 |
| 4,586,280 | 5/1986 | Dane | 2/195.1 |
| 4,985,935 | 1/1991 | Hur | 2/195.1 |
| 5,070,545 | 12/1991 | Tapia | 2/195.1 |
| 5,381,559 | 1/1995 | Wakefield, III | 2/195.1 |
| 5,410,761 | 5/1995 | Connelly et al. | 2/195.1 |

*Primary Examiner*—C. D. Crowder
*Assistant Examiner*—Larry D. Worrell, Jr.

[57] ABSTRACT

Headwear comprising a support positionable on the head of a wearer with a front positionable across the forehead of a wearer and sides positionable across the sides of the head of a wearer. A forwardly extending shield is provided. The shield has a forward end remote from the support and a rearward end adjacent to the support with lateral side edges therebetween whereby the forward end and lateral side edges form a periphery having the shape of an object and indicia correlated to the periphery. The shield may also have an internal portion within the periphery which is bendable up or down to display logos, etc., and the periphery of this portion along with indicia may also combine or make a replication. The periphery and the indica together are designed to make a replication. Further provided are mechanisms to couple the shield with the support.

8 Claims, 5 Drawing Sheets

HEADWEAR WITH SUNSHIELD

BACKGROUND OF THE INVENTION

1. Field of the Invention

The present invention relates to headwear with sunshield and more particularly pertains to headwear with a shield having a laterally enlarged central extent for increased shielding from the sun and with the shield having peripheral edges shaped as various logos or objects with correlated indicia for making a statement.

2. Description of the Prior Art

The use of headwear with sunshields of a wide variety of designs and configurations is known in the prior art. More specifically, headwear with sunshields of a wide variety of designs and configurations heretofore devised and utilized for the purpose of shaping hats and adorning them with indicia for a wide variety of purposes are known to consist basically of familiar, expected and obvious structural configurations, notwithstanding the myriad of designs encompassed by the crowded prior art which have been developed for the fulfillment of countless objectives and requirements.

By way of example, the prior art discloses in U.S. Pat. No. 1,163,054 to Williams discloses a combined eye shade and program.

U.S. Pat. No. 1,776,175 to Wittekind discloses an airplane head gear toy.

U.S. Pat. No. 4,268,918 to Lee discloses a novelty cap.

U.S. Pat. No. 4,586,280 to Dane discloses a novelty advertising cap.

Lastly, U.S. Pat. No. Des. 315,052 to Lockwood discloses a visor.

In this respect, the headwear with sunshield according to the present invention substantially departs from the conventional concepts and designs of the prior art, and in so doing provides an apparatus primarily developed for the purpose of shaping headwear with a shield having a laterally enlarged central extent for increased shielding from the sun and with the shield having a periphery shaped as an object with correlated indicia for making a statement.

Therefore, it can be appreciated that there exists a continuing need for new and improved headwear with sunshield having a laterally enlarged central extent for increased shielding from the sun and with the shield having a periphery shaped as an object with correlated indicia for making a statement. In this regard, the present invention substantially fulfills this need.

SUMMARY OF THE INVENTION

In view of the foregoing disadvantages inherent in the known types of headwear with sunshields of a wide variety of designs and configurations now present in the prior art, the present invention provides an improved headwear with sunshield. As such, the general purpose of the present invention, which will be described subsequently in greater detail, is to provide a new and improved headwear with sunshield apparatus and method which has all the advantages of the prior art and none of the disadvantages.

To attain this, the present invention essentially comprises new and improved headwear for increased shielding and for making a statement comprising, in combination, a head covering of a flexible material in a generally hemispherical configuration having a closed upper extent and a lower extent with an opening for positioning on the head of a wearer. The lower extent has a rear portion positionable over the back of a wearer's head. Side portions are positioned over the temples and sides of the wearer's head and a front portion is positionable over the forehead of a wearer's head with a central point at a central extent of the front portion. A forwardly extending shield is in a generally planar configuration with an upper surface and a lower surface and has a curved rearward end formed as a concave recess positionable adjacent to the front portion of the covering portion and has a forward end positionable forwardly of the front portion of the head covering portion and having lateral side edges therebetween whereby the forward end and side edges from a periphery. The shield has a linear central axis extending between the forward end and rearward end of the shield. The shield has a plurality of transverse lines perpendicular to the central axis including a forward transverse line extending across a forward end of the shield. A rearward transverse line extends across a rearward end of the shield and an intermediate transverse line is located between the forward and rearward lines and parallel therewith. The intermediate transverse line has a length greater than the rearward transverse line for increased shielding. Indicia is on the upper surface or both the upper and lower surfaces of the shield. The indicia is correlated to the shape of the periphery whereby the indicia and periphery together make a replication. Further provided are means of coupling together the head covering and shield.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved headwear with sunshield which may be easily and efficiently manufactured and marketed.

It is a further object of the present invention to provide a new and improved headwear with sunshield which is of a durable and reliable construction.

An even further object of the present invention is to provide a new and improved headwear with sunshield which is susceptible of a low cost of manufacture with regard to both materials and labor, and which accordingly is then susceptible of low prices of sale to the consuming public, thereby making such headwear with sunshields of a wide variety of designs and configurations economically available to the buying public.

Another object of the present invention is to provide a new and improved headwear with sunshield which provides in the apparatuses and methods of the prior art some of the advantages thereof, while simultaneously overcoming some of the disadvantages normally associated therewith.

Another object of the present invention is to shaping headwear with a shield having a laterally enlarged central extent for increased shielding from the sun and with the shield having a periphery shaped as an object with correlated indicia for making a statement.

Lastly, it is an object of the present invention to provide new and improved headwear comprising a support positionable on the head of a wearer with a front positionable across the forehead of a wearer and sides positionable across the sides of the head of a wearer. A forwardly extending shield is provided. The shield has a forward end remote from the support and a rearward end adjacent to the support with lateral side edges therebetween whereby the forward end and lateral side edges form a periphery having the shape of an object and indicia correlated to the periphery. The periphery and the indica together are designed to make a replication or statement. Further provided are mechanisms to couple the shield with the support.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

Similar reference characters refer to similar parts throughout the several views of the drawings.

DESCRIPTION OF THE PREFERRED EMBODIMENT

Figure 1:
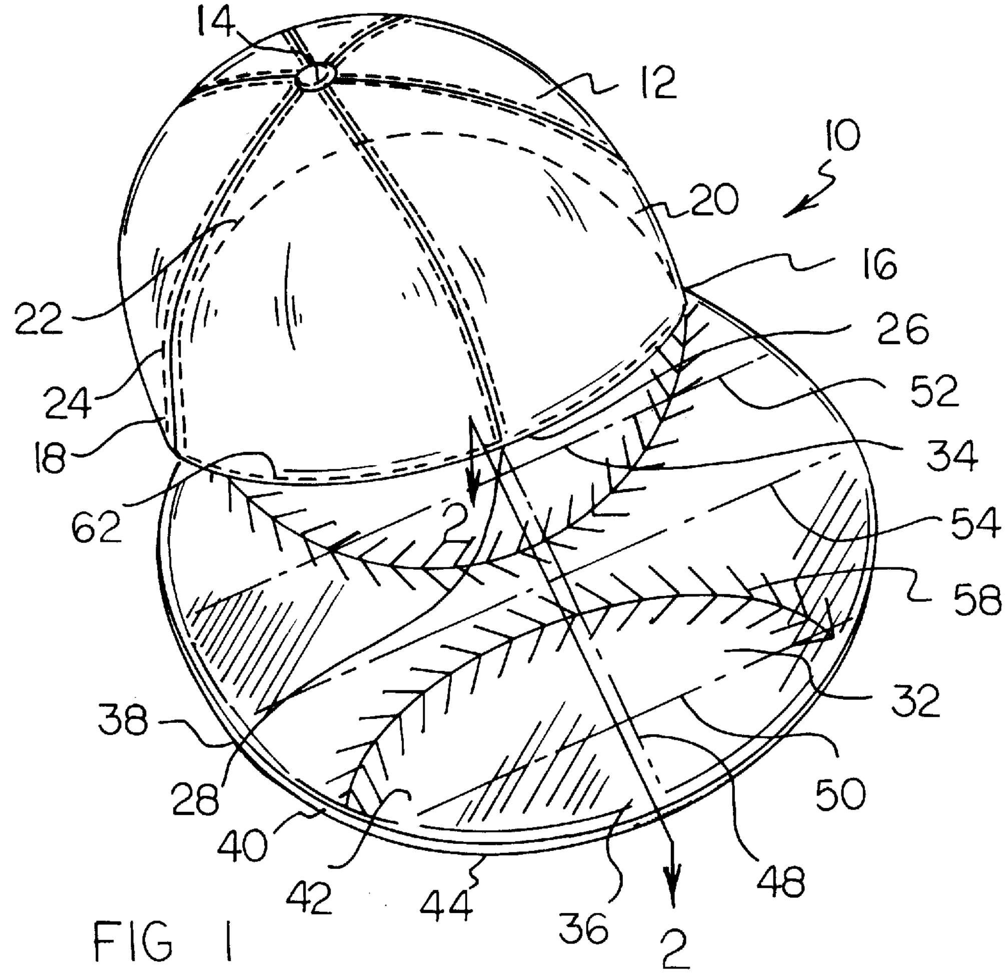
FIG. 1 is a perspective illustration of the preferred embodiment of the headwear with sunshield constructed in accordance with the principles of the present invention.

With reference now to the drawings, and in particular to FIG. 1 thereof, a new and improved headwear with sunshield embodying the principles and concepts of the present invention and generally designated by the reference numeral 10 will be described.

The present invention, the new and improved headwear with sunshield, is comprised of a plurality of components. Such components in their broadest context include a support such as a cap, a shield and coupling means therebetween. Such components are individually configured and correlated with respect to each other so as to attain the desired objective.

More specifically, one of the central components of the headwear 10 of the present invention is a support in the form of a head-covering 12. It is shaped in a generally hemispherical configuration. It has a closed upper extent 14 and an opening 16 at its lower extent 18. The opening is for positioning of the head covering on the head of a wearer. The lower extent of the head covering is positionable over the back of a wearer's head. It also has opposed side portions 24. Such side portions are positionable over the temples and sides of the wearer's head. In addition, the head covering has a front portion 26 positionable over the forehead of a wearer. The front portion has a central point 28 at a central extent of the front portion.

The next major portion of the headwear 10 of the present invention is a peak or shield 32. Such shield is for shielding the sun from the eyes of a wearer. Such shield extends forwardly from the head covering in a generally planar configuration. It has a curved rearward end 34 formed as a concave recess. Such rearward end is positionable adjacent to the front portion of the head covering portion. The shield also has a forward end 36 positioned forwardly of the front portion of the head covering. It also has lateral side edges 38 between the forward and rearward ends. The side edges and forward end form a periphery 40. In addition, the shield has an upper surface 42 and a lower surface 44.

The shield also has a linear central axis 48. Such axis extends between the forward end and the rearward end of the shield. In addition, the shield is formed to have a plurality of transverse lines perpendicular to the central axis. Such transverse lines include a forward transverse line 50 adjacent to the forward end of the shield. The transverse lines also include a rearward transverse line 52 adjacent to the rearward end of the shield. There is also included an intermediate transverse line 54 located between the forward and rearward lines and parallel with such two other lines. In the preferred embodiment, the intermediate transverse line is of a greater length than both the forward transverse line or the rearward transverse line. In this manner, extended shielding from the sun is provided to the wearer of the headwear of the present invention.

Figure 2:
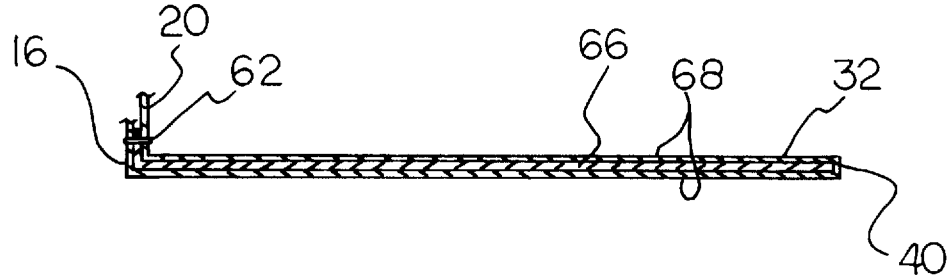
FIG. 2 is a cross-sectional view taken along line 2—2 of FIG. 1.

Printed, sewn, painted, stamped, molded or otherwise formed with respect to the shield 32 is indicia 58. Such indicia is preferably formed on the upper surface of the shield. It can also be formed on either or both upper and lower surfaces. The indicia is correlated to the shape of the periphery of the shield. In this manner, the indicia and periphery when taken together make a replication or statement. The statement of the preferred embodiment of FIGS. 1 and 2 is that of a baseball cap such that a cap will indicate a relationship of the wearer to the game of baseball due to the shape of the shield as well as the indicia of baseball stitches on the shield.

Also provided in the primary embodiment are means for coupling the shield and the head covering. In the preferred embodiment, such preferred coupling is stitching 62. Such stitching couples the head covering 12 with the shield 32. Other means of coupling such as snaps, velcro, staples, glue, etc., can be used. In such preferred embodiment, the shield can be molded or stamped of one piece or can be fabricated of an inner layer 66, as shown in FIG. 2, of a material having limited flexibility such as, preferably cardboard. Such material also allows the creasing and bending of the shield to assume other than a totally planar shape. Another material for the inner layer of the shield is plastic. Formed on the outside of the inner layer is an outer layer 68. Such outer layer 68 is preferably of a woven fabric such as cotton. It also could be any fabric, natural or synthetic, or blends thereof. It could also be fabricated of a knitted material. In the alternate, the indicia could be printed directly on the inner layer with the outer layer eliminated.

In the embodiment described above, the indicia is in the form of printing on the shield. Such printing raises the surface of the shield a negligible amount. It should be understood, however, that the indicia could take the form of thicker printing to give a distinctive visual appearance. The indicia could also take the form of a discernable elevation in the area representing the stitching or a depression in the area representing the stitching. Such may readily be done during a molding process of a plastic part. In such case, however, the raising or recessing of the indicia would be minimal, preferably less than 50 percent but might be up to 200 percent of the thickness of the shield and the shield, which is thin in itself, would still be considered an essentially planar member.

Figure 4:
FIG. 4 is another perspective illustration of the headwear of FIG. 3 but shown on a wearer.
Figure 3:
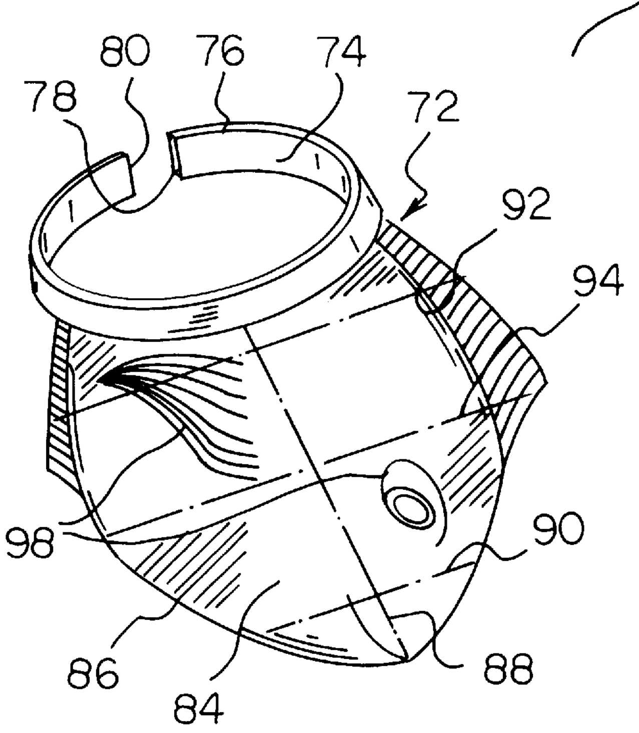
FIG. 3 is a perspective illustration of an alternate embodiment of the invention.

The second embodiment of the invention is shown in FIGS. 3 and 4. In such second embodiment, the headwear 72 is formed of a flexible material, preferably a plastic selected from the class of flexible plastics including polyethylene, polypropylene, polyvinyl chloride and like flexible plastics. The support 74 is formed not as a head covering in the primary embodiment but rather as a simple generally cylindrical support having an opening 76 at the top and an opening 78 at the bottom. The flexible side walls conform to the sides of a particular wearer's head. The shield 84 extends forwardly thereof. It has a periphery 86 in the shape of a fish. Such shape is not necessarily symmetric about a linear central axis 88 as the primary embodiment. Such embodiment does, however, have a rearward transverse line 92 as well as an intermediate transverse line 94 of a length greater than the rearward transverse line.

In the preferred mode of this alternate embodiment shown in FIGS. 3 and 4, the generally planar shield as well as the support are integrally fabricated during a common fabrication process. Such preferred fabrication process is molding in the preferred embodiment. In addition, indicia 98 in the form of parts of a fish correlated to the shape of the periphery are designed to give a statement that the wearers of the headwear of this embodiment are fisher persons. The indicia on the upper surface of the shield 84 may be molded into the upper exterior surface of the shield or maybe formed therein subsequently as by printing. Indicia may be applied to the lower surface as well. To enhance the indicia, the eye and nostril may be formed as a hole through the shield.

Figure 5:
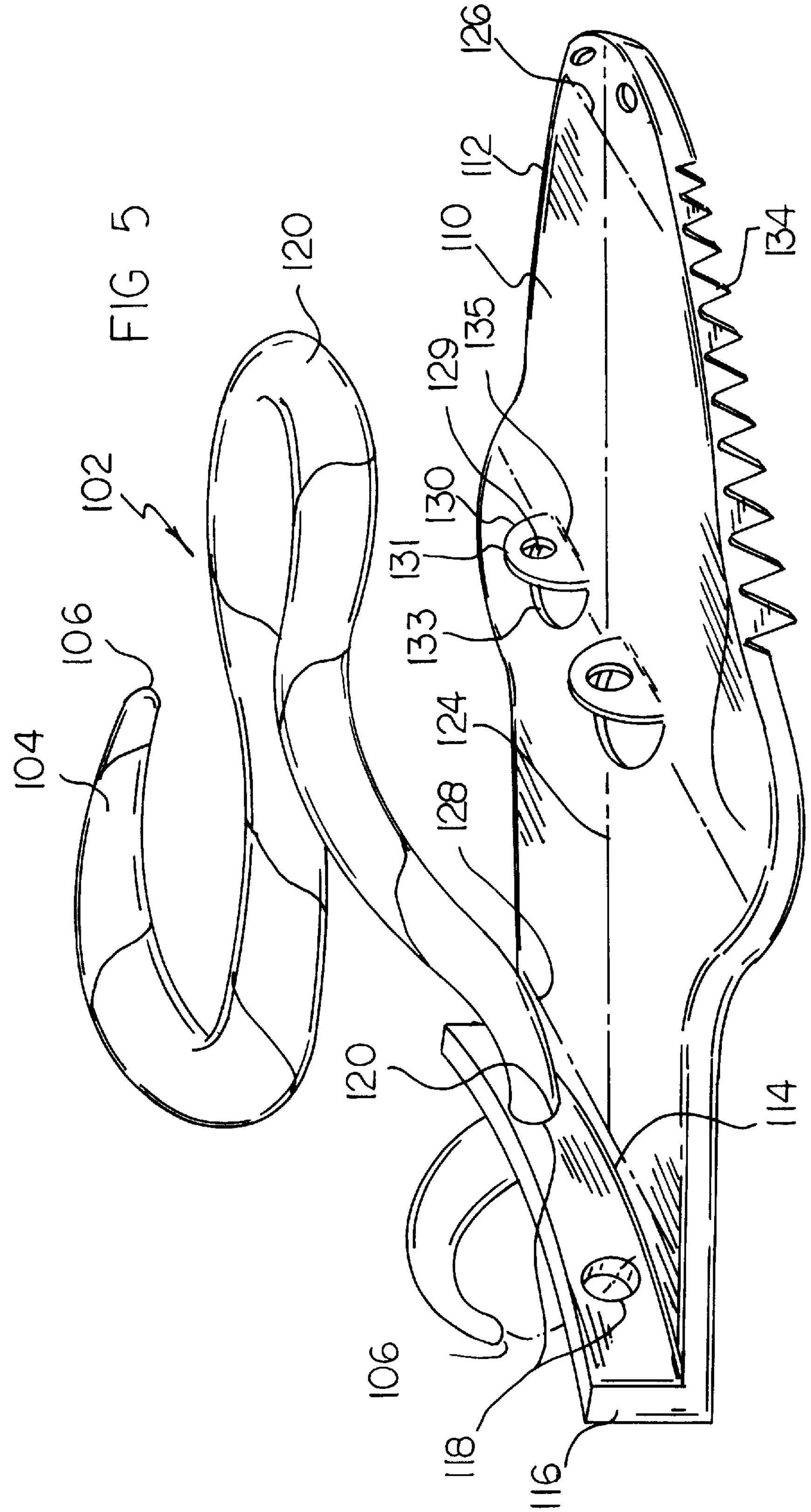
FIG. 5 is a perspective illustration of headwear constructed in accordance with a third embodiment of the invention.

The next embodiment of the invention is shown in FIG. 5. In such embodiment, the support 104 takes the form of a bandanna. Such bandanna is a rectangular piece of cloth folded at opposed edges into a triangle and then wrapped upon itself to make a rope-like configuration with free ends 106 adapted to be tied in a knot or bow at the back of a wearer's head. In such embodiment, the shield 110 is formed with a periphery 112 in the form of an alligator head. The eyes 129 are shown as apertures which are indicia but which may be other indicia such as lines or the like. The rear end 114 of the alligator head is provided with an upturned portion 116. Such upturned portion has apertures 118. Such apertures are for the receipt of the bandanna. Receipt is effected through threading one end of the bandanna through the holes in such manner that a central point 120 of the bandanna is located between the holes 118. The free ends of the bandanna can then be tied or otherwise secured behind the head of a wearer. In this embodiment of FIG. 5, the shield 110 is fabricated of one-piece plastic as in the embodiment of FIGS. 3 and 4. As in the prior embodiments, the shield has a linear central axis 124. It also has a transverse axis 126 adjacent to the forward end as well as a transverse axis 128 adjacent to the rearward end as well as an intermediate transverse axis 130. The intermediate axis, as in the prior embodiments, is located between the forward and rearward axes and parallel with both. Such intermediate transverse axis 130 is of a length greater than the rearward transverse axis. In this embodiment, the periphery of the shield is shaped as the head of an alligator while the indicia is designed to provide indications of the eyes and nostrils of an alligator.

The alligator indica of FIG. 5 preferably includes teeth 134 at a peripheral or lateral edge of the shield. Such teeth constitute at least one peripheral portion of the shield having means of bending such peripheral portion at an angle downwardly, or in some instances upwardly, to be located in a plane different from the plane of the adjacent portion of the shield. If necessary, bend lines are provided in the region wherein the bent portion couples to the adjacent portion of the shield. This arrangement is to enhance the esthetic appeal of the shield and the headwear and to add rigidity to the shield and, in some cases, may be necessary for the completion of the indicia or replication.

In this manner, one wearing the headwear of this FIG. 5 embodiment will, due to the shape of the periphery as well as the indicia on the upper surface of the shield, be indicating a preference for the team whose mascot is the alligator, the periphery and indicia being so correlated. Portion 116 may be turned downward as well as upwards.

The shield of the embodiment featuring the alligator has cut-outs 131 to constitute indicia representing the eyes of the alligator. In addition, above the eyes are essentially semi-circular separation lines 133. Such separation lines are shown as slits extending through the shield. Alternative constructions could include perforations or score lines through the visor at spaced points to assist in separating the regions of the shield on opposite sides of the separation lines. In this manner, the regions of the shield surrounding the eyes may be bent upwardly for a greater visual impact. Movement upwardly is preferably facilitated through bend lines 135. Such bend lines are shown as dots of depressions but could readily be dots of cuts partially or fully through the shield to indicate the area where the bending is to occur and to effect the bending.

Figure 6:
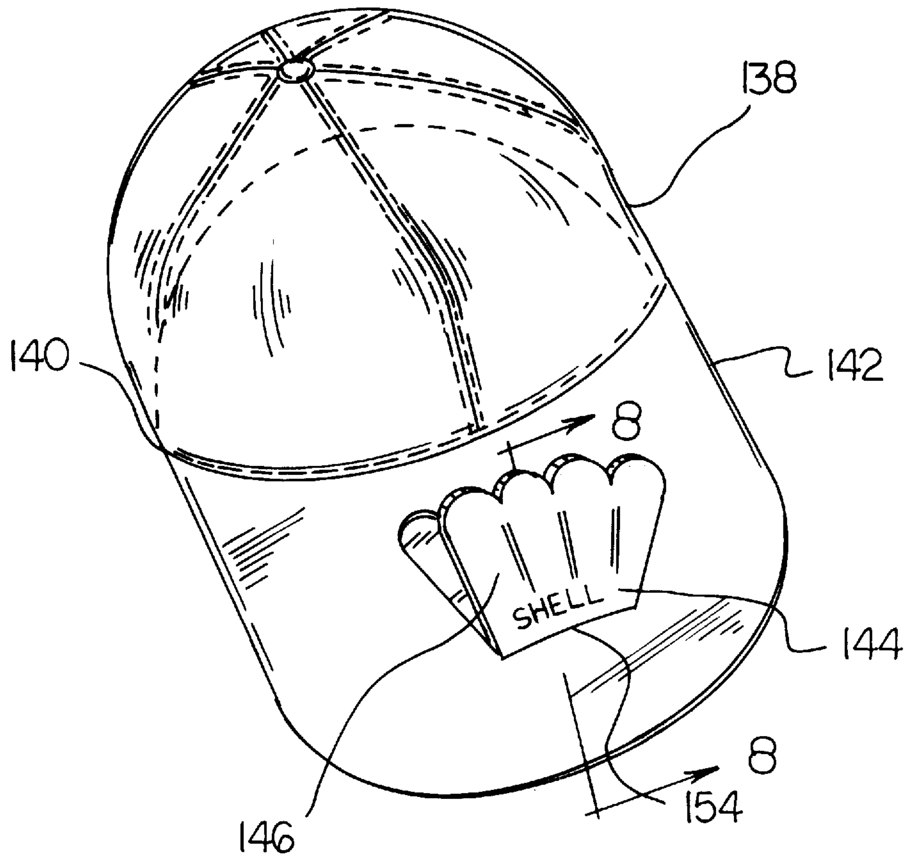
FIG. 6 is a perspective illustration of headwear constructed in accordance with a fourth and final embodiment of the invention.
Figure 7:
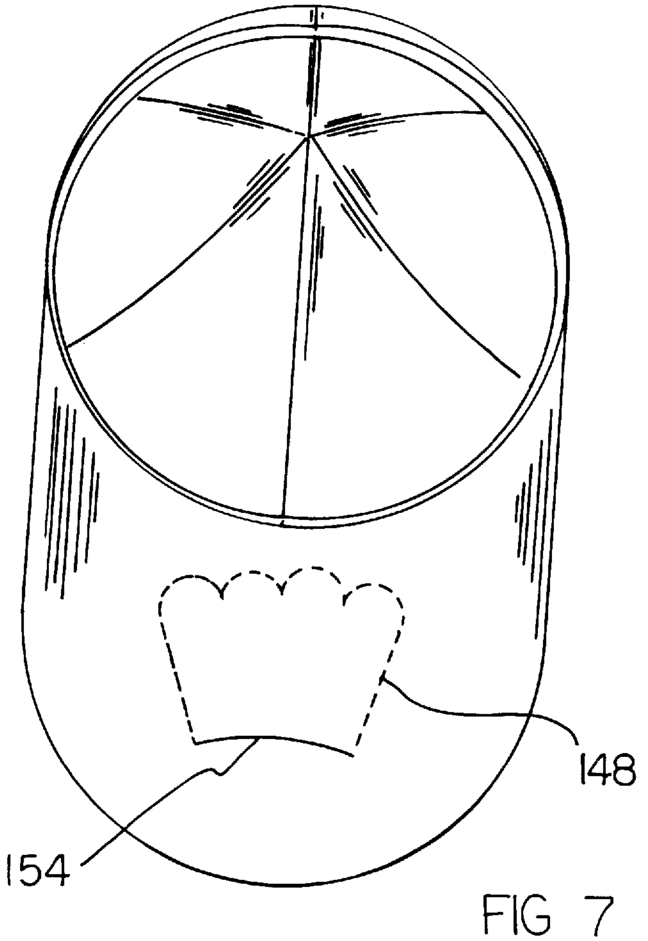
FIG. 7 is a bottom plan view of the shield shown in FIG. 6.

In the fourth and final embodiment of the invention, that is shown in FIGS. 6 and 7, the headwear 138 includes a support 140. The shield includes exterior peripheral edges 142 as in the primary embodiment. The shield also includes a portion with secondary peripheral edges 144. Such edges are formed through a cut-out or pop-up portion 146. The pop-up includes a separation line 148 taking the form of a sea-shell or scallop. In addition, indicia 150 in the forms of lines of printing further provide distinctiveness. In such case, the outwardly flared lines are on the upper face of the pop-up but may readily be provided on both sides of the pop-up portion 146 for viewing from either side. Additional indicia 152 is also provided in the form of a corporate logo. As in the immediately prior embodiment, the separation line 148 may take the forms of slits, perforations or score lines or the like when the separation is totally through upon manufacture or wherein the separation may be readily effected by the user or another. In addition, this fourth embodiment includes a bend line 154. The bend line may be dots of cuts or a depressed line as in the immediately prior embodiment. In the present embodiment, however, the bend line is preferably formed not linear as in the prior embodiment but in a slight curve to facilitate retention of the pop-up portion in its erect orientation.

Figure 8:
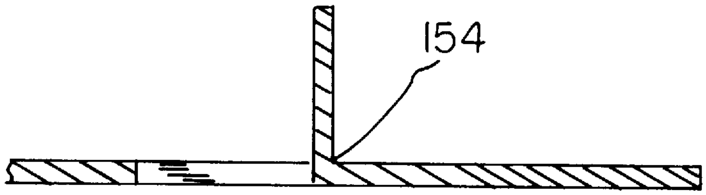
FIG. 8 is a side elevational view of the hat of FIGS. 6 and 7 but with the pop-up element erect.

In the disclosed embodiment of FIGS. 6–8, the pop-up section is a sea shell with lines on one side. The shell, with or without lines, is considered indicia, a corporate identifier. The outline of the shell by itself is also considered herein to be indicia. Other forms of indicia, as the term is used herein are numerals, letters, ideographs, symbols and the like where the shape of the edges of the identifier convey identifiable information.

It should be understood that the shapes as described above are for illustrative purposes only. The shapes of the exterior shield peripheries and the interior pop-up peripheries within the shield may take a very wide variety of configurations. Such shapes include logos, balls, mascots such as animals, containers such as cans, jewelry, boxes and bottles, food, whether natural or prepared, including candy, fruit, vegetables, communication devices such as televisions, radios, computers, telephones, vehicles such as boats, cars and trucks, tubes or plants, whether artificial or natural. As stated above, such shapes are for illustrative purposes only and are only constrained by the imagination.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved headwear for increased shielding and for making a statement comprising, in combination:

a head covering of a flexible material in a generally hemispherical configuration having a closed upper extent and a lower extent with an opening for positioning on the head of a wearer, the lower extent having a rear portion positionable over the back of a wearer's head, side portions positioned over the temples and sides of the wearer's head and a front portion positionable over the forehead of a wearer's head and with a central point at a central extent of the front portion;

a forwardly extending shield in a generally planar configuration with an upper surface and a lower surface and having a curved rearward end formed as a concave recess positionable adjacent to the front portion of the covering portion and having a forward end positionable forwardly of the front portion of the head covering portion and having lateral side edges therebetween whereby the forward end and side edges form a periphery, the shield having a linear central axis extending between the forward end and rearward end of the shield, the shield having a plurality of transverse lines transverse and perpendicular to the central axis including a forward transverse line extending across a forward end of the shield, a rearward transverse line extending across a rearward end of the shield and an intermediate transverse line located between the forward and rearward lines and parallel therewith, the intermediate transverse line having a length greater than the rearward transverse line for increased shielding each of the transverse lines extending continuously across the entire shield;

indicia on the upper surface or both the upper and lower surfaces of the shield, the indicia being correlated to the shape of the periphery whereby the indica and periphery together make a replication; and means coupling the head covering and shield.

2. Headwear comprising:

a support positionable on the head of a wearer with a front positionable across the forehead of a wearer and sides positionable across the sides of the head of a wearer;

a forwardly extending shield, the shield having a forward end remote from the support and a rearward end adjacent to the support, the shield also having lateral edges forming a shape of an object and printed indicia located between the lateral edges correlated to the shape of the lateral edges, the shape of the lateral edges and the indicia together being designed when viewed together to make a common replication, the shield having a linear central axis extending between the forward end and rearward end of the shield, the shield having a plurality of transverse lines transverse and perpendicular to the central axis including a forward transverse line extending across a forward end of the shield, a rearward transverse line extending across a rearward end of the shield and an intermediate transverse line located between the forward and rearward lines and parallel therewith, the intermediate transverse line having a length greater than the rearward transverse line for increased shielding each of the transverse lines extending continuously across the entire shield; and means to couple the shield with the support.

3. The headwear as set forth in claim 2 wherein the support is a head covering of flexible material in a generally hemispherical configuration having a closed upper extent and an opening at its lower extent for positioning on the head of a wearer, the lower extent having a rear portion positionable over the back of a wearer's head.

4. The headwear as set forth in claim 2 wherein the shield separably couples with respect to the support.

5. The headwear as set forth in claim 2 wherein the support is open at the top.

6. The headwear as set forth in claim 2 wherein the support is a bandanna kerchief.

7. The headwear as set forth in claim 2 wherein the shield's lateral edges are curved with a concave recess at the rearward end and the indicia is in the form of distinctive markings of various sport balls.

8. The apparatus as set forth in claim 2 wherein the support and shield are fabricated of plastic and fabricated integrally with each other.

* * * * *